United States Patent [19]

Davitz

[11] 4,038,074
[45] July 26, 1977

[54] METAL ALLOY COMPOSITION
[75] Inventor: Daniel M. Davitz, Niles, Ill.
[73] Assignee: Astro, Niles, Ill.
[21] Appl. No.: 706,473
[22] Filed: July 19, 1976
[51] Int. Cl.$^2$ .............................................. C22C 19/05
[52] U.S. Cl. ..................................................... 75/171
[58] Field of Search .................... 75/171, 170; 148/32, 148/32.5

[56] References Cited

U.S. PATENT DOCUMENTS 3,841,868  10/1974  Dudek et al. ........................... 75/171

Primary Examiner—R. Dean
Attorney, Agent, or Firm—Hibben, Noyes & Bicknell, Ltd.

[57] ABSTRACT

A nickel-chromium based alloy comprised of nickel, chromium, molybdenum, cobalt, silicon and boron to which tin and indium is added as essential alloying elements to provide markedly improved fluidity, castability, workability and adhesion to porcelain with lighter oxide filed without impairing the strength and resistance of the alloy to deformation. The combination of properties makes the alloy particularly useful as a dental alloy for making bridges, crowns and inlays and for casting jewelry.

4 Claims, No Drawings

METAL ALLOY COMPOSITION

The present invention relates generally to metallic alloys and more particularly to non-precious metal alloys having chemical and physical properties which make the alloy useful for casting articles having intricate details and especially useful for the making of dental structures, such as dental bridges, crowns and inlays.

When casting metal articles having intricate design details, such as required in the manufacture of jewelry and dental bridges, crowns and inlays, it is highly desirable that the metal have a relatively low melting point and form a highly fluid melt which is capable of flowing into the smallest openings of a mold. And, when solidified the metal casting should exhibit high tensile strength, good resistance to deformation and should be capable of being readily worked and polished. It is important that the material used for casting dental fittings when solidified have good adhesion for sintered and fused silicate material, such as porcelain and other ceramic, glass and plastic materials. Good resistance to corrosion and attack by mouth acids is also important in metal alloys used in the manufacture of dental fittings.

Heretofore various corrosion resistant non-precious metal alloys have been developed to replace precious metals for use by the dental profession. Several of these non-precious metal alloys are comprised of nickel, chromium, molybdenum and cobalt to which minor amounts of other alloying elements, such as beryllium, have been added. The presence of beryllium in the alloy, however, creates toxicity problems during the preparation, handling and use of the alloys. Consequently, these beryllium-containing alloys are not entirely satisfactory for either metallurgical or dental applications. Moreover, none of these alloys possess all the properties desired in a dental alloy or in an alloy for replacing the precious metals used for making intricate castings.

It is therefore an object of the present invention to provide a metal alloy having chemical and physical properties which make the alloy better suited for casting intricate structures, such as jewelry, and for use in the manufacture of dental bridges, crowns and inlays and the like dental structures.

It is a further object of the present invention to provide a nickel-chromium based corrosion resistant alloy which exhibits increased fluidity and improved castability compared with alloys of this type heretofore made.

It is another object of the present invention to provide a nickel-chromium based alloy which has greater adhesion to porcelain and other fused and sintered silicate materials than alloys of this type heretofore made.

It is still another object of the present invention to provide a nickel-chromium based alloy which when heated to an elevated temperature in contact with a ceramic material forms a thinner, lighter oxide layer than alloys of this type heretofore made.

It is also an object of the present invention to provide a nickel-chromium based alloy which has good tensile strength, good impact resistance while also possessing the capability of being worked and polished with conventional finishing tools without the inclusion of beryllium in the alloy.

A still further object of the present invention to provide a nickel-chromium based dental alloy with good tensile strength and impact resistance while also having a softness less than natural dentition so that the alloy does not wear down the natural tooth surfaces in contact therewith.

Other objects of the present invention will be apparent to one skilled in the art from the following detailed description and accompanying claims.

The objects of the present invention are achieved by combining with the heretofore known ingredients of a nickel-chromium based alloy comprising nickel, chromium, molybdenum, cobalt and silicon, a combination of critical metal additives consisting of tin and indium, and preferably with a small amount of boron and iron when the boron is added as ferro-boron. The addition of tin and indium to an alloy containing nickel and chromium with relatively small amounts of molybdenum, silicon and cobalt produces low melting point nickel-chromium base alloys having highly desirable properties heretofore unobtainable in a non-precious metal alloy by imparting thereto significantly improved fluidity and castability, increased adhesion to a porcelain surface with a thinner, lighter oxide layer, and a softer, smoother grained casting having improved workability without impairing the strength and resistance of the alloy to permanent deformation. These desirable properties make the alloy particularly suitable for use in casting intricate structures, including jewelry and dental fittings.

The alloys of the present invention having improved properties over the precious and non-precious metal alloys heretofore made have a chemical analysis on a weight percent basis falling within the following ranges:

|  | Range | |
| --- | --- | --- |
| Nickel | 63.0 – | 74.8 |
| Chromium | 17.0 – | 21.9 |
| Molybdenum | 2.5 – | 5.0 |
| Cobalt* | 1.0 – | 5.0 |
| Silicon | 2.0 – | 3.0 |
| Tin | 1.0 – | 5.0 |
| Indium | 0.5 – | 2.0 |
| Boron | 1.00 – | 3.00 |
| Copper | 0.00 – | 5.00 |
| Iron | 0.005 – | 1.00 |

*Cobalt can be replaced by Paladium

A preferred embodiment of the improved alloy of the present invention has the following chemical analysis on a weight percent basis:

| Nickel | 67.9 |
| --- | --- |
| Chromium | 17 |
| Molybdenum | 3.5 |
| Cobalt | 3 |
| Silicon | 2.5 |
| Tin | 4 |
| Indium | 1 |
| Boron | 1.05 |
| Iron | .05 |

The preferred alloy composition has a Brinell hardness of 226, a Vicker's hardness of 235, a tensile strength of 52,120 psi, a Young's Modulus of $24.1 \times 10^6$ lbs./sq. in., and a specific gravity of 8.25.

Among the important characteristics of the alloys of the present invention which distinguish these alloys over the nickel-chromium based alloys heretofore made is the unusually high fluidity of the alloys at a relatively low temperature. Thus, the preferred alloy composition of the present invention melts at a temperature of 2200° F (1204° C) and can be cast at a temperature of 2300° F (1260° C). At the foregoing casting temperature the preferred alloy composition has such a high fluidity that, if desired, the alloy can be successfully vacuum cast. The unusually high fluidity property enables the alloys of the present invention to fill extremely small openings within a mold and avoids having the mold incompletely filled.

A further distinguishing characteristic of the alloys of the present invention is their unusual adhesion or affinity to porcelain, other ceramics, glass and plastic materials. When a Pyrex glass button, for example, is heated in contact with the surface of the above-mentioned preferred alloy, the Pyrex button must be broken before it can be separated from the alloy surface. This property of unusually strong adhesion to a sintered of fused silicate-containing material makes these alloys particularly useful for producing dental bridges, crowns and inlays or other denture structures which require providing a porcelain or like facing thereon.

A still further property which makes the alloy particularly useful in the dental profession is the high oxidation resistance of the alloy when heated to an elevated temperature in contact with a porcelain or other ceramic material, as when preparing a dental bridge or crown. It has been found, for example, that at the interface between the alloy surface and the porcelain coating a very thin oxide layer is formed which has a light color in contrast with the thick dark colored oxide layer normally formed when the nickel-chromium based alloys heretofore known are heated while in contact with porcelain. By avoiding forming a thick dark oxide layer when preparing a dental bridge or crown, for example, there is less space between the alloy surface and the porcelain into which mouth fluids can enter and ultimately destroy the oxide layer and breakage of the porcelain. Also, the bridge or crown will not have a dark lower edge formed thereon and thus provide a dental fitting having a more esthetic appearance.

The non-precious metal alloys of the present invention also have the unusual property of being softer and more workable than the non-precious metal alloys heretofore made and in general have many physical properties similar to the precious metals. For example, the nickel-chromium based alloys containing tin and indium in the indicated amounts have a softness such that they are softer than natural dentition and will not wear down the tooth structure brought into contact therewith.

The present alloys, per se, also have good tissue compatability, resist attack by mouth acids and can be polished with conventional finishing tools without flaking. It will thus be evident that the alloys of the present invention possess all the essential properties required of a superior dental alloy, such as the gold base alloys, and in addition possess superior tensile strength, resistant to deformation and have a specific gravity substantially less than the gold base alloys so that a lighter, stronger dental fitting can be made.

In preparing the alloy compositions of the present invention it has been found that the boron component can be best incorporated into the alloy by using ferroboron rather than metallic boron. When unalloyed boron is used substantially larger amounts of boron are required in order to obtain the desired level of boron in the final alloy. Thus, unalloyed boron must be used in the make-up charge at a level of about 3% by wt., whereas only about 1% by wt. ferro-boron is required to provide the desired boron content.

It has also been found that the bonding strength or adhesion of the oxide layer of the alloy can be further improved by including a small amount of copper, preferably about 0.25 wt. % copper. Since the addition of copper to the alloy has the further property of increasing the hardness of the alloy, the amount of copper added to a dental alloy should be carefully limited. For other uses of the alloy where softness is not required, up to about 5 wt. % copper can be included in the alloy before brittleness becomes objectionable.

In using the alloys of the present invention for making a dental fitting a suitable quantity of the alloy is melted to form a puddle at a temperature of 2200° F and is heated to a casting temperature of 2300° F by an oxygen-air torch using only 6-10 lbs. oxygen pressure. It is advisable to use the same amount of metal which would normally be used when using a precious metal, as too much of a button could cause porosity. The molten metal at a temperature of 2300° F is then poured into any ceramic investment mold. The alloy flows very much like the precious metals. The investment mold is preferably formed by the lost wax technique with the wax pattern being burned out at a temperature of 1350° F for about 60 minutes. The poured alloy is then centrifugally cast, and after casting the solidified alloy is removed from the mold and the casting finished using an aluminum oxide stone.

The casting is porcelainized preferably after vacuum degassing at 1825° F, cleaning the surfaces with alcohol or clean water, and sand blasting the finished casting to roughen its surface, followed by washing the surfaces with clean water. A layer of opaque porcelain is applied under vacuum according to the manufacturer's instructions, and the manufacturer's instructions should be followed for the porcelain application. The dental fitting is finished with steel or carbide burrs or mounted stones and can be treated very much like a dental fitting made from a precious metal. Polishing or burnishing is effected by means of an extra hard rubber wheel and final polishing with a chrome polishing compound provides a highly lustrous surface.

I claim:

1. An alloy having a chemical analysis on a weight percent basis consisting essentially of:

| | | | |
|---|---|---|---|
| Nickel | 63.0 | – | 74.8 |
| Chromium | 17.0 | – | 21.9 |
| Molybdenum | 2.5 | – | 5.0 |
| Cobalt | 1.0 | – | 5.0 |
| Silicon | 2.0 | – | 3.0 |
| Tin | 1.0 | – | 5.0 |
| Indium | 0.5 | – | 2.0 |
| Boron | 1.00 | – | 3.00 |
| Copper | 0.00 | – | 5.00 |
| Iron | 0.005 | – | 1.00 | said alloy having a melting point of about 2200° F (1204° C) and a casting temperature of about 2300° F (1260° C), and said alloy being characterized by a lower melting point, a lower casting temperature, a higher fluidity at said casting temperature, greater adhesion for a sintered silicate-containing materials and for a fused silicate glass materials and a softer more workable surface than the alloy would otherwise have without the said tin and indium.

2. An alloy of claim 1, wherein said alloy on a wt. percent basis consists essentially of:

| | |
|---|---|
| Nickel | 67.9 |
| Chromium | 17 |
| Molybdenum | 3.5 |
| Cobalt | 3 |
| Silicon | 2.5 |
| Tin | 4 |
| Indium | 1 |
| Boron | 1.05 |
| Iron | .05 |

3. An alloy as in claim 2, wherein said alloy contains 0.25 wt. percent copper.

4. An alloy as in claim 1, wherein said alloy contains paladium in place of the said cobalt.

* * * * *